United States Patent [19]

Kobayashi et al.

[11] Patent Number: 5,206,318

[45] Date of Patent: Apr. 27, 1993

[54] STYRENE DERIVATIVES HAVING N-ACETYLCHITO-OLIGOSACCHARIDE CHAINS AND METHOD FOR THE SAME

[75] Inventors: Kazukiyo Kobayashi, Aichi; Toshihiro Akaike, Tokyo; Hosei Shinoda, Aichi; Kazushi Morimoto, Chiba, all of Japan

[73] Assignee: Mitsui Toatsu Chemicals, Inc., Tokyo, Japan

[21] Appl. No.: 855,159

[22] Filed: Mar. 20, 1992

Related U.S. Application Data

[63] Continuation of Ser. No. 510,583, Apr. 18, 1990, abandoned.

[30] Foreign Application Priority Data

Apr. 20, 1989 [JP] Japan ................................. 1-98839

[51] Int. Cl.$^5$ .............................................. C08B 37/08
[52] U.S. Cl. ............................ 526/238.23; 526/238.2; 526/238.3; 536/18.7; 536/20; 536/30
[58] Field of Search ...................... 536/20, 30, 18.7; 526/238.2, 238.3

[56] References Cited

U.S. PATENT DOCUMENTS

| | | | |
|---|---|---|---|
| 4,169,079 | 9/1979 | Tabushi et al. | |
| 4,356,236 | 10/1982 | Kosaugi | 428/403 |
| 4,699,135 | 10/1987 | Motosugi | 530/356 |
| 5,021,201 | 6/1991 | Eguchi | 264/9 |

FOREIGN PATENT DOCUMENTS 0282623 9/1988 European Pat. Off.

OTHER PUBLICATIONS

Kobayashi, Kazukiyo, Polymer Journal, vol. 15, No. 9 pp. 667–671 (1983) A Carbohydrate-Containing Synthetic Polymer Obtained from N-p-vinylbenzyl-D--gluconamide.

Polymer Journal, vol. 15, No. 9, pp. 667–671, 1983.

Chemical Abstracts, vol. 103, No. 2, Abstract No. 6 784a, 1985.

*Primary Examiner*—Joseph L. Schofer
*Assistant Examiner*—F. Zitomer
*Attorney, Agent, or Firm*—Burns, Doane, Swecker & Mathis

[57] ABSTRACT

A styrene derivative carrying N-acethylchito-oligosaccharide chains, a polystyrene derivative carrying N-acetylchito-oligosaccharide chains on the side chains as well as a method for preparing these compounds are herein disclosed. The method for preparing the styrene derivative comprises reacting N-acetylchito-oligosaccharide lactone with vinylbenzylamine or a derivative thereof while the method for preparing the polystyrene derivative comprises polymerizing the styrene derivative. These derivatives can be employed as biomedical materials, in particular as materials for cell culture.

5 Claims, No Drawings

STYRENE DERIVATIVES HAVING N-ACETYLCHITO-OLIGOSACCHARIDE CHAINS AND METHOD FOR THE SAME

This application is a continuation of application Ser. No. 07/510,583 filed Apr. 18, 1990, now abandoned.

BACKGROUND OF THE INVENTION

The present invention relates to styrene derivatives and polystyrene derivatives used as biomedical substances, in particular materials for cell culture as well as a method for preparing these derivatives.

Owing to the progress in cell culture techniques, considerable progress has been made in studies on the mechanisms of proliferation, differentiation, aging, oncogenesis or the like of cells. In addition, biologically active substances such as vaccins, hormones and interferons have correspondingly been produced. Moreover, it is expected that the production of biological artificial organs such as artificial livers, blood vessels and skin could be developed on the basis of experimental results on culture of various cells such as liver cells, blood vessel wall cells and fibroblast cells of the skin. It is very important to cultivate cells for the purpose of allowing cells to develop a variety of their functions in vitro for a long period of time.

Liver cells by way of an example is specifically explained in more detail to make this point clear. The liver is the greatest glanderous organ of vertebrate animals and is a metabolic center which performs most part of metabolism and regulation thereof. The liver cells originally have long life time over several years and potential ability of proliferation so that they can actively proliferate when a part thereof is accidentally removed. However, if they are cultured in vitro, the life time thereof is greatly shortened, they show almost no proliferation ability and their metabolic activity is rapidly reduced. In general, the culture of cells requires the use of a solid surface to which the cells are adhered when they are cultivated. The liver cells hardly adhere to the surface of usually employed culture dishes of glass or polystyrene which have been surface-treated. Therefore, it has long been desired to develop biomedical materials which make it possible to cause adhesion and proliferation of these cells while maintaining the functions thereof.

Recently, as the mechanisms of cell adhesion, of information transmission through a cell membrane or the like are elucidated at molecular level, it has become clear that sugar chains which exist on the surface of cell membranes in the forms of glycoproteins or glycolipids play an important role in recognizing ability of the cells.

The inventors of this invention already synthesized polystyrenes having monosaccharide or oligosaccharide residues such as glycose, maltose, lactose and maltotriose residues on the side chains and tried to adhere rat liver cells to the surface of a culture dish to which a film of such a polystyrene had been applied. As a result, it is found that the polystyrene film having lactose residues on the side chains, among others, substantially increases the ability of the liver cells to adhere to the surface of a culture dish irrespective of the presence of serum. Thus, these polymers show excellent properties as hybrid type biomedical materials (see "Japanese Journal of Polymer Science and Technology", 1985, Vol. 42, No. 11, pp. 719-724).

As explained above, these polystyrenes having monosaccharide or oligosaccharide residues on the side chains show excellent cell-recognizing ability. As a result, they make it possible to cause good adhesion and proliferation of specific cells such as liver cells. However, they do not serve to adhere and proliferate other cells. For this reason, it has been desired to develop various biomedical materials which exhibit ability of adhering and proliferating other cells and hence have wide variety of applications.

SUMMARY OF THE INVENTION

Accordingly, an object of the present invention is generally to provide novel biomedical materials, in particular to those which would have cell-recognizing ability and ability of adhering various cells.

Another object of the present invention is to provide a novel styrene derivative carrying N-acetylchito-oligosaccharide chains, which can provide polystyrene derivatives having good cell-adhesion and cell-proliferation ability.

A further object of the present invention is to provide a polystyrene derivative having N-acetylchito-oligosaccharide chains on the side chains, which has wide applications as biomedical materials.

A still further object of the present invention is to provide methods for preparing such novel biomedical materials.

The inventors of this invention have conducted various studies to achieve the foregoing objects, have found that a novel styrene derivative can be obtained by reacting a derivative of N-acetylchito-oligosaccharide with a vinylbenzylamine or a derivative thereof and that a novel polymer can be prepared by polymerizing the styrene derivative and thus have completed the present invention.

The present invention thus relates to a styrene derivative having N-acetylchito-oligosaccharide chains and a polystyrene derivative having N-acetylchito-oligosaccharide chains on the side chains as well as a method for preparing these compounds.

DETAILED EXPLANATION OF THE INVENTION

The present invention will hereunder be described in more detail.

The term "N-acetylchito-oligosaccharide chain(s)" herein used means sequences represented by the following general formula (7):

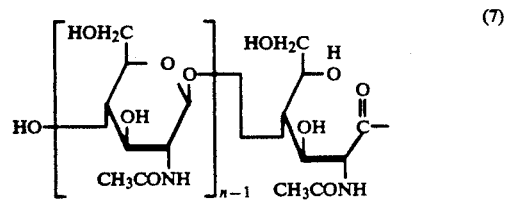

(7)

(wherein n is an integer ranging from 1 to several tens and preferably 1 to 10).

The N-acetylchito-oligosaccharides are hydrolyzates of chitin. Chitin is represented by the following general formula (8):

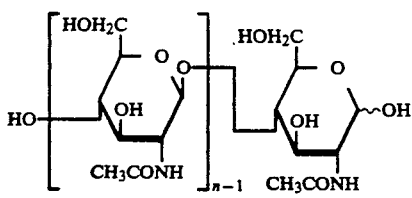

(8)

(wherein n is an integer ranging from 1 to several tens and preferably 1 to 10). It is a kind of aminosaccharide in which D-glucosamine whose amino groups are acetylated is bonded through a β (1→4) bond, is a component constituting the outer coat-skeletal structure of lower animals such as cell walls of Crustacea, Insecta, Shellfish, Fungi and is a biological resources whose amount of production is comparable to that of cellulose ($10^{11}$ tons/year). In addition to such abundance of chitin as a natural resource, chitin is not only excellent in bioabsorbability and in biocompatibility, but also shows ability of healing wound openings and is correspondingly, a polysaccharide having possibility of wide variety of applications as a biomedical material.

Moreover, if chitin is decomposed into low molecular weight substances or converted into oligosaccharides, the resulting low molecular weight substances show improved properties such as antibacterial properties, biodegradability, biological activity.

The monosaccharide, N-acetylglycosamine, constituting chitin is a sugar which is naturally universally occuring as a component of various substances such as glycoproteins, glycolipids, proteoglycans, lipopolysaccharides and peptidoglycans and which is closely involved in biorecognition and biological activity.

Therefore, compounds carrying chitin chains or N-acetylchito-oligosaccharide chains and their polymers are useful as novel biomedical materials.

The styrene derivatives carrying N-acetylchito-oligosaccharide chains according to the present invention can be prepared according to the following procedures. First, N-acetylchito-oligosaccharide which is a precursor of the derivative can be obtained through partial hydrolysis of chitin. The precursor may have any degree of polymerization ranging from 1 to several tens, but it has preferably the degree of polymerization of up to 10 from the viewpoint of the reactivity thereof or the like.

The hydroxyl group present at 1-position of the N-acetylchito-oligosaccharide is oxidized with a proper oxidizing agent to give N-acetylchito-oligosaccharide lactone represented by the following general formula (5):

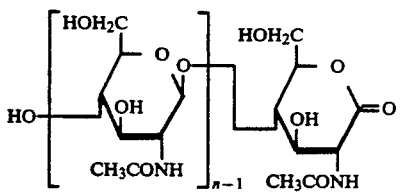

(9)

(wherein n is an integer ranging from 1 to several tens, preferably 1 to 10).

Any known oxidizing agents may be employed in the oxidation reaction of the N-acetylchito-oligosaccharide. However, if a extremely strong acid is used, the hydroxymethyl group present at 6-position is also oxidized. Thus, preferred are mild oxidizing agents such as iodine or bromine. Further, any reaction solvents may be used so far as they can solubilize the N-acetylchito-oligosaccharide and the oxidizing agent used. Preferred examples of such reaction solvents are water and water/methanol mixed solvent.

The styrene derivatives carrying N-acetylchito-oligosaccharide chains according to the present invention can be prepared by reacting the aforementioned N-acetylchito-oligosaccharide lactone with a vinylbenzylamine or a derivative thereof.

Methanol is preferably employed as a reaction solvent when the N-acetylchito-oligosaccharide lactone is reacted with vinylbenzylamine or a derivative thereof.

Examples of the foregoing vinylbenzylamine derivatives are those having substituents such as lower alkyl groups at the α-position and/or the β-position of the vinyl group and those having substituents such as lower alkyl groups, lower alkoxy groups, hydroxyl group, halogen atoms, alicyclic groups on the benzene ring.

Examples of the vinylbenzylamine and derivatives thereof which are reacted with the N-acetylchito-oligosaccharide lactone are preferably those represented by the following general formula (6):

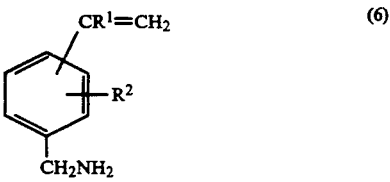

(6)

(wherein $R^1$ represents a hydrogen atom or a methyl group; and $R^2$ represents a hydrogen atom, a lower alkyl group, a lower alkoxy group or a halogen atom).

Thus, preferred styrene derivatives carrying N-acetylchito-oligosaccharide chains according to the present invention are those represented by the following general formula (1):

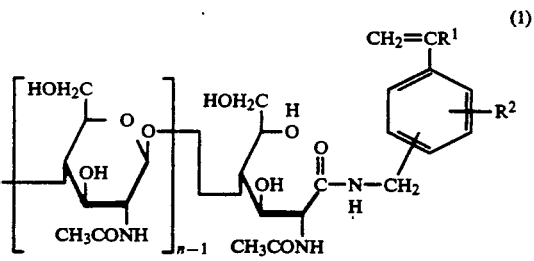

(1)

(in the general formula (1), $R^1$ represents a hydrogen atom or a methyl group; $R^2$ represents a hydrogen atom, a lower alkyl group, a lower alkoxy group or a halogen atom; and n is an integer ranging from 1 to 10).

The vinylbenzylamines and derivatives thereof used may be in either of p-, m- and o-conformations and preferably the p-isomer is employed. p-Vinylbenzylamine is prepared, for instance, through a reaction of N-p-vinylbenzylphthalimide with hydradine hydrate as disclosed in Polymer Journal, 1983, 15, p. 667.

The styrene derivatives carrying N-acetylchito-oligosaccharide chains obtained according to the present invention are novel compounds and their structures can be identified, for instance, in terms of nuclear magnetic resonance spectrometry and/or infrared spectrometry. The styrene moiety thereof is linked to the N-acetylchito-oligosaccharide chain through the bond: —CH$_2$— NH— and the derivatives may be in either of p-, m- and o- conformations. For instance, when p-vinylbenzylamine is reacted with an N-acetylchito-oligosaccharide lactone represented by the general formula (5) wherein n is an integer ranging from 1 to 10, a styrene derivative represented by the following general formula (2).

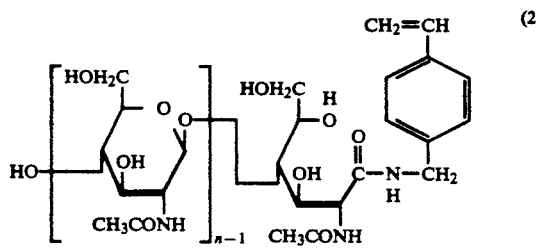

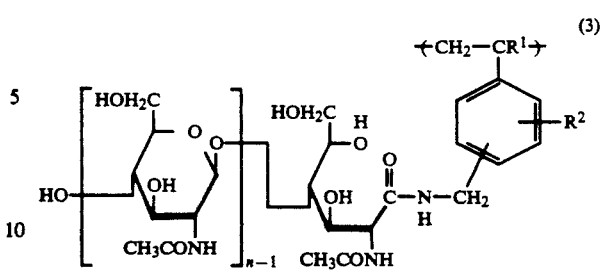

(wherein n is an integer of 1 to 10) can be obtained. These derivatives are particularly preferred in the present invention.

The polystyrene derivatives carrying N-acetylchito-oligosaccharide chains on the side chains according to the present invention can be obtained by polymerizing the styrene derivatives having N-acetylchito-oligosaccharide chains according to the present invention.

The polystyrene derivatives carrying N-acetylchito-oligosaccharide chains on the side chains according to the present invention may also comprise repeating units derived from other copolymerizable vinyl compounds such as styrenes in addition to those derived from the styrene derivatives having N-acetylchito-oligosaccharide chains. Examples of such styrenes usable in the invention include styrene, α-methylstyrene and p-hydroxystyrene. If the polystyrene derivatives are copolymers, they should contain not less than 5 mol% of the styrene derivative carrying N-acetylchito-oligosaccharide chain in order to exhibit ability of adhering and proliferating cells. They may be obtained by copolymerizing 5 to 100 mol% Of the styrene derivative carrying N-acetylchito-oligosaccharide chains with 0 to 95 mol% of other vinyl monomers.

Any polymerization solvents may be used so far as they can solubilize monomers such as styrene derivatives carrying N-acetylchito-oligosaccharide chains and other styrenes, but preferred are water and dimethylsulfoxide.

The polymerization is performed in the presence of a polymerization catalyst such as those known as polymerization catalysts for styrenes. Preferred catalysts are radical initiators such as potassium persulfate, azobisisobutyronitrile and 2,2'-azobis(amidinopropane) hydrochloride.

The polymerization temperature is appropriately determined depending on the kinds of the catalysts used and the amount thereof and preferably it ranges from about 0° to about 90° C.

Preferred examples of the polystyrene derivatives having N-acetylchito-oligosaccharide chains on the side chains according to the present invention are those having 2 to 500 repeating units represented by the following general formula (3):

(in the general formula, R$^1$ represents a hydrogen atom or a methyl group; R$^2$ represents a hydrogen atom, a lower alkyl group, a lower alkoxy group or a halogen atom; and n is an integer ranging from 1 to 10).

If the repeating units are more than 500, the polystyrene derivatives have a tendency to decrease solubility of the polystyrene derivatives in water or other solvents.

Particularly preferred examples of the polystyrene derivatives having N-acetylchito-oligosaccharide chains on the side chains according to the present invention are those represented by the following general formula (4):

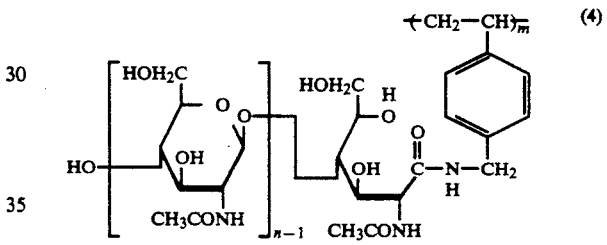

(wherein n is an integer ranging from 1 to 10 and m is an integer ranging from 2 to 500).

The present invention will be described in more detail with reference to the following non-limitative working Examples and the effects practically achieved by the invention will also be discussed in detail in comparison with Comparative Examples. In the following Examples, physical properties or the like are determined as follows:

Infrared (IR) spectra:

This is measured according to potassium tablet method;

Nuclear Magnetic Resonance Spectra ($^{13}$C-NMR):

This is measured on a specimen obtained by dissolving each sample in heavy water containing about 1% of methanol (concentration=about 10%);

Angle of Rotation:

This is determined at 25° C., each sample being dissolved in water (concn.=1 g/100 ml) and D-line of sodium as a light source and a polarimeter being employed.

REFERENCE EXAMPLE 1

Preparation of N-Acetylchito-oligosaccharide Lactone:
[0-β-2-acetamido-2-deoxy-D-glucopyranosyl-(1→4 ]$_{n-1}$-1-2-acetamido-2-deoxy-D-gluconolactone; Formula (5); hereunder referred to as "AGL"

2.1 g of N-acetylchito-oligosaccharide (a mixture of 3-, 4- and 5-mers thereof; average degree of polymerization=3.3 to 4.0) was dissolved in 100 ml of water and then 75 ml of a 0.1N aqueous iodine solution and 75 ml of a 0.1N aqueous potassium hydroxide solution were slowly dropwise added to the resulting solution. A 0.1N aqueous solution of potassium hydroxide was further dropwise added thereto till the color of the free iodine disappeared. After the concentration of the reaction solution to several ml, the concentrate was poured into 150 ml of methanol and stirred. The resultant while precipitates were collected by centrifugation, dried in vacuo and dissolved in 10 ml of water. 0.1 g of silver carbonate was added and the solution was stirred. The resulting dark gray precipitates were removed by filtration and the filtrate was passed through a column packed with Amberlite IR-120. The fractions were concentrated under a reduced pressure and then dissolved in methanol. Thereafter, ethanol was added to the solution and it was evaporated to dryness, which were repeated three times. The product was dried in vacuo to give yellowish white powder. The product was identified to be AGL in terms of IR and $^{13}$C-NMR spectroscopic measurements.

EXAMPLES 1 to 5

Preparation of
N-p-vinylbenzyl-(O-β-2-acetamido-2-deoxy-D-glucopyranosyl-(1→4)
$_{n-1}$-2-acetamido-2-deoxy-D-gluconamide; Formula (2); hereunder referred to as "VGNA"

As listed in the following Table 1, a desired amount of AGL was dissolved in methanol (MeOH) and/or dimethylsulfoxide (DMSO) and a methanolic solution of p-vinylbenzylamine was added to the solution to react these at a desired temperature for a desired time. After the concentration of the reaction solution, the concentrate was dissolved in water and was washed several times with chloroform. The water phase was concentrated, the concentrate was poured into acetone and the resultant while powder was separated and recovered. White powder obtained after being dried was washed with methanol and acetone, was dissolved in water and lyophilized to give VGNA as yellowish white powder.

IR (cm$^{-1}$): 3400 (O—H stretching); 2920 (C—H stretching); 1640 (amido C—O stretching); 1540 (amido N—H deformation).

$^{13}$C-NMR(δ ppm): 174.6 (carbonyl C of acetamido group); 172.1 (carbonyl C of vinylbenzylamido group); 114.5 to 137.5 (C of benzene ring and vinyl group); 101.5 (β anomer C of chito-oligosaccharide); 55 to 80 (C of oligosaccharide residue); 22.3 (methyl C of acetamido group).

Degree of Rotation [α]: +0.2°.

TABLE 1

| Ex. No. | AGL (*1) (g) | VBA(*2) (g) | MeOH (ml) | DMSO (ml) | Temp. (°C.) | Time (hr.) | Yield (%) |
|---|---|---|---|---|---|---|---|
| 1 | 1.0 | 0.34 | 10 | 10 | R.T. | 48 | 38 |
| 2 | 1.0 | 0.34 | 10 | 10 | 50 | 24 | 44 |
| 3 | 2.5 | 1.20 | 20 | 20 | R.T. | 48 | 34 |
| 4 | 2.0 | 0.64 | 20 | 20 | R.T. | 96 | 40 |
| 5 | 4.5 | 1.33 | 0 | 35 | R.T. | 48 | 48 |

*1: N-acetylchito-oligosaccharide lactone: (O-β -2-acetamido-2-deoxy-D-glucopyranosyl- (1 → 4)$_{n-1}$ -2-acetamido-2-deoxy-D-gluconolactone.
*2: p-vinylbenzylamine; R.T.: room temperature.

EXAMPLES 6 to 9

The same procedures used in Example 1 were repeated except that o-vinylbenzylamine, m-vinylbenzylamine, p-α-methylvinylbenzylamine or p-vinyl-m-methylbenzylamine was substituted for p-vinylbenzylamine to obtain a styrene derivative. In each case, the yield of he styrene derivative was 13%, 21%, 32% or 28%.

EXAMPLES 10 to 14

As listed in the following Table 2, desired amounts of VGNA and 2,2'-azobis(2-amidinopropane)-hydrochloride (catalyst) were introduced into a test tube for polymerization and was dissolved in water. A cock for deaeration was fixed to the tube, freezing and deaeration operations were repeated three times and then the tube was sealed by heating. After polymerization at 60° C. for a desired time, the tube was opened and the resulting reaction solution was poured into methanol. White powder precipitated out was filtered off, dissolved in water and reprecipitated from methanol, this cycle being repreated three times. The powder obtained was again dissolved in water and was introduced into a cellulose tube to perform dialysis against water for 3 days. The dialyzed solution was concentrated and lyophilized to give a polymer.

IR(cm$^{-1}$): 3400 (O—H stretching); 2930 (C—H stretching); 1640 acetamido C—O stretching); 1549 (amido N—H deformation).

$^{13}$C-NMR(δ ppm): 174.4 (carbonyl C of acetamido group); 172.0 (carbonyl C of vinylbenzylamido group); 145.1, 135.5, 128.3 (C of benzene ring); 101.1 (β anomer C of chito-oligosaccharide); 55 to 80 (C of oligosaccharide residue); 41.6 (methylene C of polystyrene chains and benzyl group); 22.3 (methyl C of acetamido group).

TABLE 2

| Ex. | VGNA DPn (*2) | (*1) (g) | Cat. (*3) (mol %) | Water (ml) | Temp (°C.) | Time (hr.) | Yield (%) | Rot. (deg.) |
|---|---|---|---|---|---|---|---|---|
| 10 | 3.3 | 0.96 | 0.1 | 12 | 60 | 2 | 17 | +1 |
| 11 | 3.3 | 0.82 | 0.2 | 6 | 60 | 10 | 20 | −2 |
| 12 | 3.3 | 0.82 | 0.2 | 3 | 60 | 10 | 30 | — |
| 13 | 3.3 | 0.82 | 0.1 | 3 | 60 | 6 | 46 | −1 |
| 14 | 4.0 | 0.96 | 0.2 | 3 | 60 | 12 | 63 | — |

*1: N-p-vinylbenzyl-(O-β -2-acetamido-2-deoxy-D-glucopyranosyl-(1 → 4)$_{n-1}$-2-acetamido-2-deoxy-D-gluconamide
*2: average degree of polymerization of N-chito-oligosaccharide chain.
*3: 2,2'-azobis(2-amidinopropane)-hydrochloride.
Rot.: degree of rotation.

EXAMPLE 15

The same procedure used in Example 10 was repeated except that a styrene derivative obtained in Example 8 by using p-α-methylvinylbenzylamine was used as a starting monomer to obtain a polystyrene derivative. In this case, the yield of the polystyrene derivative was 12%.

EXAMPLE 16

The VGNA polymer (PVGNA) obtained in Example 14 was dissolved in distilled water (conc.: 1%) and the solution was magnetically stirred at room temperature for 4 days. After the filtration thereof through a Millipor filter, 1 ml thereof was poured into a culture dish (polystyrene; φ 100 mm) and allowed to stand at room temperature for 10 minutes to adsorb the polymer onto the surface of the culture dish. The supernatant was removed and the dish was rinsed three times with 1 ml of a phosphate buffer to coat the surface of the culture dish with the polymer.

10 ml of DME culture medium containing 5% FCS was added to the culture dish and mouse C 127 cells were inoculated so that the population of the cells were 500/dish. The dish was incubated in a culture device whose carbon dioxide concentration was adjusted to 5% to cultivate the cells at 37° C. for 2 weeks. Then the cells (colony) growing on the culture dish was stained with Crystal Violet to confirm the growth condition and the number of colonies of the cells. The results observed are summarized in the following Table 3.

Thus, it is found that the culture dish to which the polystyrene carrying N-acetylchito-oligosaccharide chains on the side chains was applied makes it possible to cause good adhesion and proliferation of mouse C127 cells.

COMPARATIVE EXAMPLES 1 to 4

The same cell adhesion-experiments performed in Example 16 were carried out using culture dishes to which polystyrenes each having lactose, melibiose or maltose residues on the side chains (hereunder referred to as PVLA, PVMeA and PVMA respectively) were applied (Comparative Examples 1, 2 and 3 respectively) and a commercially available culture dish of polystyrene (Falcon 1001; for general bacteria) free of polymer coat (Comparative Example 4). The results thus obtained are listed in the following Table 3.

TABLE 3

| Ex. No. | Coated Polymer | Growth Condition | Number of Colony |
|---|---|---|---|
| 16 | PVGNA | good | 163 |
| 1* | PVLA | incomplete | 3 |
| 2* | PVMeA | " | 9 |
| 3* | PVMA | " | 7 |
| 4* | — | " | 1 |

*Comparative Example.

As explained above in detail, according to the present invention, there are provided novel styrene derivatives carrying N-acetylchito-oligosaccharide chains and novel polystyrene derivatives having N-acetylchito-oligosaccharide chains on the side chains serving as novel biomedical materials as well as a method for preparing these novel compounds. The polystyrene derivatives of the present invention show excellent ability of adhering and proliferating mouse C127 cells and thus can be effective as biomedical materials.

What is claimed is:

1. A styrene including chains comprising N-acetylchito-oligosaccharide chains.

2. A styrene according to claim 1 represented by the following general formula (1):

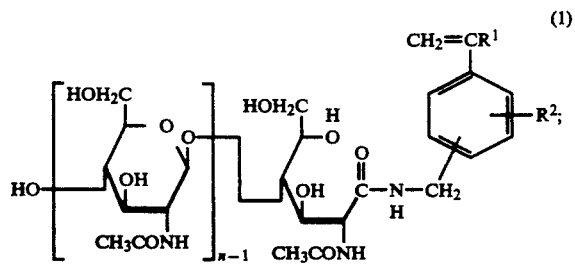

wherein $R^1$ represents a hydrogen atom or a methyl group; $R^2$ represents a hydrogen atom, a lower alkyl group, a lower alkoxy group or a halogen atom; and n is an integer ranging from 1 to 10.

3. A styrene according to claim 2 represented by the following general formula (2):

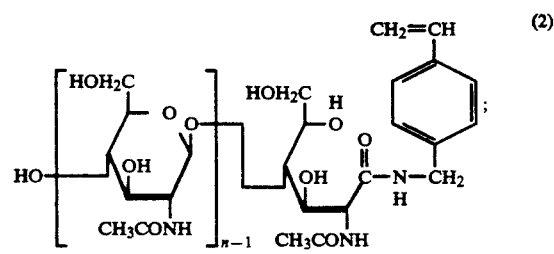

wherein n is an integer of 1 to 10.

4. A polystyrene comprising 2 to 500 of repeating units represented by the following general formula (3):

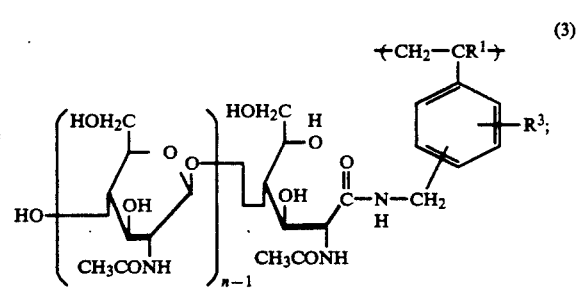

wherein $R^1$ represents a hydrogen atom or a methyl group; $R^2$ represents a hydrogen atom, a lower alkyl group, a lower alkoxy group or a halogen atom; and n is an integer ranging from 1 to 10.

5. A polystyrene according to claim 4 represented by the following general formula (4):

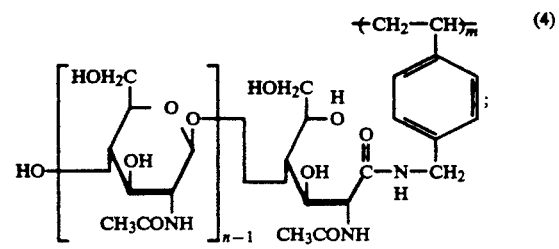

wherein n is an integer ranging from 1 to 10 and m is an integer ranging from 2 to 500.

* * * * *